United States Patent
Herrmann

(10) Patent No.: US 10,231,678 B2
(45) Date of Patent: Mar. 19, 2019

(54) PET-CT SYSTEM WITH SINGLE DETECTOR

(75) Inventor: Christoph Herrmann, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1251 days.

(21) Appl. No.: 13/884,978

(22) PCT Filed: Nov. 15, 2011

(86) PCT No.: PCT/IB2011/055081
§ 371 (c)(1),
(2), (4) Date: May 13, 2013

(87) PCT Pub. No.: WO2012/066469
PCT Pub. Date: May 24, 2012

(65) Prior Publication Data
US 2013/0237818 A1    Sep. 12, 2013

Related U.S. Application Data

(60) Provisional application No. 61/415,140, filed on Nov. 18, 2010.

(51) Int. Cl.
*A61B 6/00* (2006.01)
*A61B 6/03* (2006.01)
(Continued)

(52) U.S. Cl.
CPC .............. *A61B 6/032* (2013.01); *A61B 6/037* (2013.01); *A61B 6/4417* (2013.01);
(Continued)

(58) Field of Classification Search
CPC ......... H01L 31/113; G01T 1/20; A61B 6/037; A61B 6/32
(Continued)

(56) References Cited

U.S. PATENT DOCUMENTS 6,448,559 B1    9/2002 Saoudi et al.
7,180,074 B1 *  2/2007 Crosetto .................. 250/370.09
(Continued)

FOREIGN PATENT DOCUMENTS

KR    20090126850 A    12/2009
WO    2004095069 A1    11/2004
(Continued)

OTHER PUBLICATIONS

Limousin. New trends in CdTe and CdZnTe detectors for X- and gamma-ray applications. 2003 Nucl.Instr.Met.Phys.Res. A 504:24-37.*

(Continued)

*Primary Examiner* — Tse W Chen
*Assistant Examiner* — Patrick M Mehl

(57) ABSTRACT

A radiation detector (16) having a first detector layer (24) and a second detector layer (26) encircles an examination region (14). Detectors of the first layer include scintillators (72) and light detectors (74), such as avalanche photodiodes. The detectors of the second detector layer (26) include scintillators (62) and optical detectors (64). The scintillators (72) of the first layer have a smaller cross-section than the scintillators (62) of the second layers. A group, e.g., nine, of the first layer scintillators (72) overlay each second group scintillator (62). In a CT mode, detectors of the first layer detect transmission radiation to generate a CT image with a relatively high resolution and the detectors of the second layer detect PET or SPECT radiation to generate nuclear data for reconstruction into a lower resolution emission image. Because the detectors of the first and second layers are aligned, the transmission and emission images are inherently aligned.

18 Claims, 6 Drawing Sheets

(51) Int. Cl.
*G01T 1/20* (2006.01)
*G01T 1/24* (2006.01)
*G01T 1/161* (2006.01)

(52) U.S. Cl.
CPC .......... *G01T 1/1611* (2013.01); *G01T 1/1612* (2013.01); *G01T 1/1614* (2013.01); *G01T 1/2018* (2013.01); *G01T 1/248* (2013.01); *A61B 6/4028* (2013.01); *A61B 6/4233* (2013.01); *A61B 6/4291* (2013.01); *A61B 6/5229* (2013.01)

(58) Field of Classification Search
USPC ........................................................ 600/436
See application file for complete search history.

(56) References Cited

U.S. PATENT DOCUMENTS

| | | | |
|---|---|---|---|
| 7,366,279 B2* | 4/2008 | Edic et al. | ......................... 378/7 |
| 2004/0066909 A1 | 4/2004 | Lonn et al. | |
| 2006/0023832 A1 | 2/2006 | Edic et al. | |
| 2006/0081899 A1* | 4/2006 | Fritzler et al. | ................. 257/291 |
| 2007/0263764 A1* | 11/2007 | Mccallum et al. | ............. 378/19 |
| 2011/0017918 A1 | 1/2011 | Baeumer et al. | |

FOREIGN PATENT DOCUMENTS

| | | |
|---|---|---|
| WO | 2009115956 A2 | 9/2009 |
| WO | 2009154340 A1 | 12/2009 |

OTHER PUBLICATIONS

Beigelman-Aubry et al. Multi-Detector Row CT and Postprocessing Techniques in the Assessment of Diffuse Lung Disease. 2005 RadioGraphics 25:1639-1652.*
Berard et al. CT Acquisition Using PET Detectors and Electronics. 2005 IEEE Trans. Nucl. Scie. 52:634-637.*
Cao et al._A dynamic micro-CT scanner based on a carbon nanotube field emission x-ray source. 2009 Phys. Med. Biol. 54:2323-2340.*
Chen et al. Determination of the system matrix used in List-Mode EM reconstruction of PET. 2007 IEEE Nucl.Sci.Symp.Conf. Record M19-219:3855-3858.*
Frutschy et al. X-ray Multisource for Medical Imaging. 2009 Proc. SPIE 7258: 725822-1-725822-12.*
Inadama et al. 8-Layer DOI encoding of 3-dimensional crystal array. 2006 IEEE Trans. Nucl. Sci. 53:2523-2528.*
Martinez et al. PET and PET/CT: Basic Principles and Instrumentation. In "PET in Oncology" series Recent Results in Cancer Research. 2008 vol. 170 Springer-Verlag Berlin Chapter 1 p. 1-23.*
Powolny et al. A Novel Time-Based Readout Scheme for a combined PET-CT detector using APDs. 2008 IEEE Trans. Nucl. Scie. 55:2465-2474.*
Zaidi et al. Advances in multimodality molecular imaging. 2009 J. Med. Phys. 34:122-128.*
Fontaine, R., et al.; Architecture of a Dual-Modality, High-Resolution, Fully Digital Positron Emission Tomography/Computed Tomography (PET/CT) Scanner for Small Animal Imaging; 2005; IEEE Trans. on Nuclear Science; 52(3) 691-696.
Lecomte, R.; Novel detector technology for clinical PET; 2009; Eur. J. Nucl. Med. Mol. Imaging; 36(Suppl 1)S69-S85.

* cited by examiner

PET-CT SYSTEM WITH SINGLE DETECTOR

CROSS REFERENCE TO RELATED APPLICATIONS

This application is a national filing of PCT application Serial No. PCT/IB2011/055081, filed Nov. 15, 2011, published as WO 2012/066469 A1 on May 24, 2012, which claims the benefit of U.S. provisional application Ser. No. 61/415,140 filed Nov. 18, 2010, which is incorporated herein by reference.

The following relates to the medical arts, medical imaging arts, medical diagnostic arts, positron emission tomography (PET) imaging arts, computed tomography (CT) arts, and related arts.

The use of positron emission tomography (PET), single photon emission computed tomography (SPECT), and other imaging modalities in oncological diagnosis, assessment, and treatment planning is increasing. PET and SPECT entail administering a radiopharmaceutical to the subject (for example, a human or animal subject) and detecting radiation emitted from the subject by the radiopharmaceutical. The radiopharmaceutical may be tailored to preferentially collect in the bloodstream or in other anatomical regions of interest so as to provide image contrast for those regions. PET and SPECT are recognized as complementary to transmission computed tomography (CT) or magnetic resonance (MR) for oncology, because PET and SPECT tend to provide functional information relating to metabolic activity; whereas, CT and MR provide primarily structural information.

Typically, the oncological specialist uses CT images to delineate a cancerous tumor and neighboring "critical structures" such as neighboring radiation-sensitive organs. An intensity modulated radiation therapy (IMRT) plan is generated based on the delineated features, and is applied using a linear accelerator ("linac") or other radiation therapy system. PET or SPECT images are generally used as supplementary data, to provide functional information such as standardized uptake value (SUV), assess any observable necrosis or metastasis, and so forth. PET and SPECT can sometimes be superior to CT for detection tasks such as detecting an initial malignant tumor or lesion or detecting the presence and rate of metastasis of the cancer, because the functional sensitivity of PET can cause nascent tumors or lesions to appear as bright spots reflecting high local metabolism.

The patient is then moved to a PET/CT or SPECT/CT scanner to generate functional data. Great care is taken to position the subject in the same location in both the CT and the PET or SPECT scanner. Misalignment of even 1 mm or less can cause significant registration errors.

The patient is injected with the radiopharmaceutical and one or more functional images are reconstructed. A PET image typically has lower resolution than a CT image, for example, each voxel may be about 4 mm$^3$. During the PET reconstruction, the CT image is used as an attenuation map to correct the PET or for attenuation.

In various applications, such as oncology, the functional and PET images are combined or fused. Because the functional image carries substantially no structural or anatomical information and the CT image provides substantially no functional information, there are substantially no commonalities between the anatomical and functional images which can be used to register them. Rather, accurate registration typically relies upon accurate placement of the patient in the two scanners. Thus, even a small amount of misalignment in the patient placement can cause significant registration errors in the combined or fused image.

The following provides new and improved apparatuses and methods which overcome the above-referenced problems and others.

In accordance with one aspect, a radiation detector is provided which has at least a first layer of detectors and at least a second layer of detectors. The detectors of the first layer have a first cross-sectional dimension that converts incident radiation from a transmission radiation source into transmission data. The detectors of the second detector layer have a second cross-sectional dimension that is different from the first cross-sectional dimension and are disposed below the first detector layer to convert emission radiation into nuclear data, such as functional or emission data.

In accordance with another aspect, a method is provided in which transmission radiation is converted into transmission data at first detectors of a first detector layer. Each of the first detectors has a first cross-sectional dimension. Emission radiation is converted into nuclear data at second detectors of a second detector layer. Each second detector has a cross-sectional dimension which is larger than the first cross-sectional dimension. The second detector layer is disposed below the first detector layer.

One advantage resides in a more efficient scanning system for both PET and CT imaging.

Another advantage resides in improved and simplified registration, since the patient does not have to be moved on the couch.

Another advantage resides in providing reduction in cost for hybrid PET-CT systems, since parts of the detector for CT are reused for PET.

Further advantages will be apparent to those of ordinary skill in the art upon reading and understanding the following detailed description.

FIG. 1 diagrammatically shows a hybrid imaging system having a single radiation detector and a rotating x-ray source and scatter grid;

Figure 1:
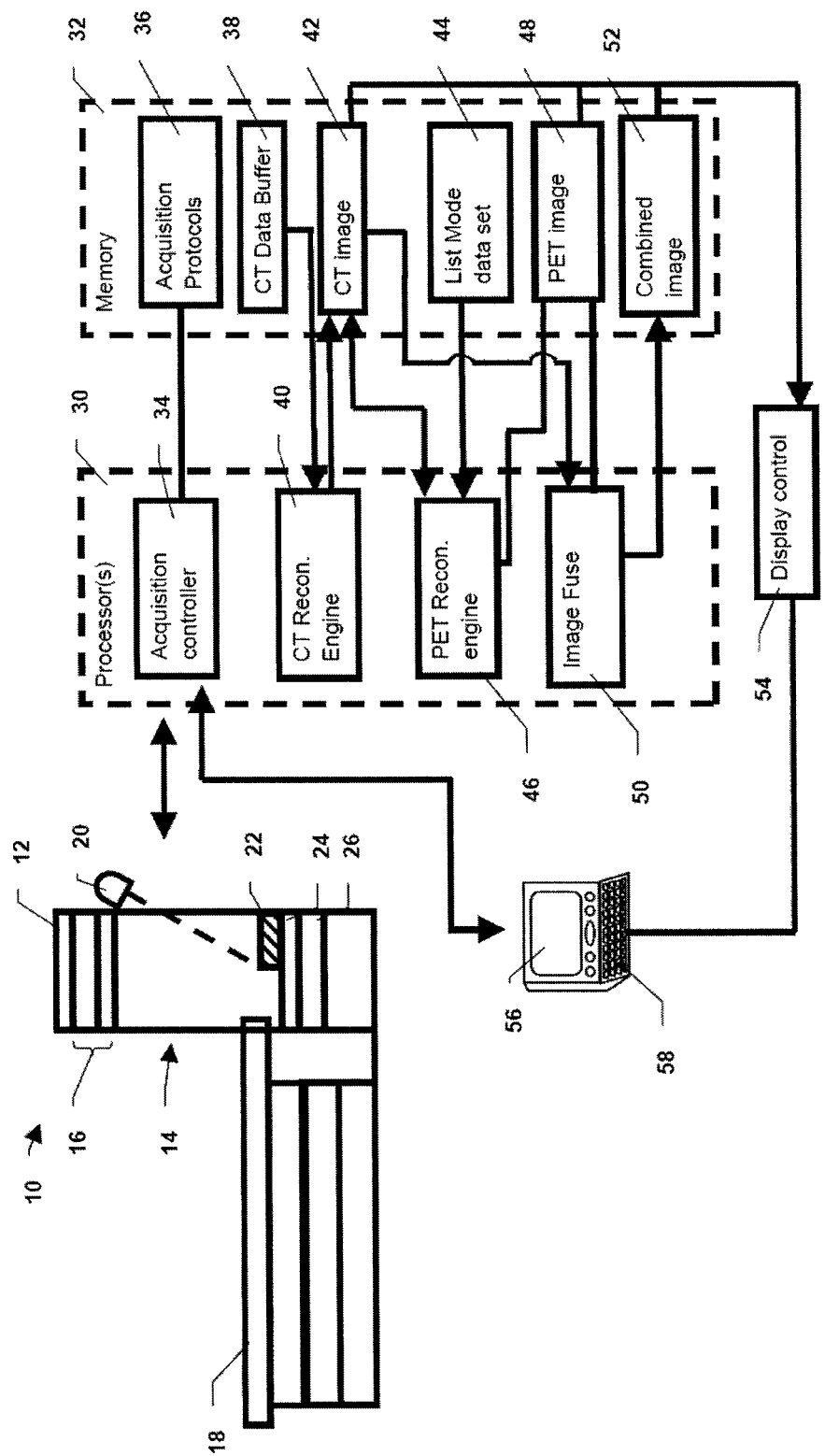

With reference to FIG. 1, a hybrid imaging system 10 includes a single gantry 12 which defines an examination region 14 therein. A ring of radiation detectors is disposed around the examination region to detect radiation which has been emitted by or has traversed a patient or other subject on a patient support 18 when it is extended into the examination region. In the embodiment of FIG. 1, a transmission radiation source 20, such as an x-ray tube, and an anti-scatter grid (also called a scatter rejecting collimator) 22 are disposed for rotation around the examination region 14. In one embodiment, the anti-scatter grid is removable from the examination region during a PET, SPECT, or other nuclear scan to acquire function or emission data (e.g., nuclear data). The anti-scatter grid is an array of vanes, each of which is in alignment with a focal spot of the x-ray source such that the detector array receives radiation which is passed directly from the radiation source through the anti-scatter grid, but radiation from other directions is blocked.

The transmission radiation source 20 typically generates x-rays with an energy of 20-140 keV; whereas, the gamma rays detected in PET imaging have an energy of 511 keV, while in SPECT imaging it is 141 keV. The detector array 16 has a first layer of detectors 24 of a thickness which captures substantially all of the CT radiation events and at least a second detector layer 26 which has a thickness such that it captures substantially all of the PET radiation events. The gantry 12 is connected with one or more processors 30 which, in turn, are connected with one or memories 32. An acquisition controller 34 accesses an appropriate CT acquisition protocol 36 from the memory 32. The acquisition controller 34 controls the gantry and x-ray source to generate CT data which is stored in a CT data buffer 38 and reconstructed by a CT reconstruction engine or algorithm 40 into a CT image representation 42 which is stored in the memories.

The acquisition controller accesses the acquisition protocols 36 to retrieve an appropriate PET imaging protocol which is used to control the gantry to generate a list mode data set 44 which a PET reconstruction engine 46 reconstructs into a PET image 48. The term "list mode" is intended to encompass any format for storing the PET data events including energy, time, and location information. In the list mode, all of the radiation events are retained in a list. During the PET data reconstruction, data from the CT image 42 is used as an attenuation map to perform attenuation correction on the list mode PET data.

An image processor 50 combines the CT and PET images to generate a combined image 52 which is stored in the memory 32. Various types of combined or fused images are contemplated as are known in the art. A video or other display controller 54 causes a display 56 to display the combined, PET, CT, or other images and combinations thereof. A keyboard or other input device 58 is used by an operator to select among the various image options and to control the acquisition controller 34 to select among the various imaging protocols. The one or more imaging facility memories 32 can include one or more magnetic storage media, one or more optical storage media, one or more electrostatic storage media, or so forth. Some illustrative examples include: a hard disk or other internal storage device or devices of the one or more computers 24; an external hard drive; a redundant array of independent disks (RAID) system; a remote Internet storage facility; or so forth. The one or more imaging facility memories 32 may also include or have access to a picture archive and communication system (PACS) maintained by a hospital or other organization owning or associated with the medical imaging facility.

In one embodiment, each single radiation detector 60 includes a scintillator and an array of SiPMs that generate digital signals for processing. SiPMs are pixelated sensors that include a highly segmented array of single avalanche photodiodes cells operating in Geiger mode. The digital SiPMs support time-of-flight for the PET-CT hybrid system and allows for radiation detection by sampling an optical signal with a high sampling frequency. This is further described in WO 2009/115956 (published 24 Sep. 2009) incorporated herein by reference in its entirety and describes that digital SiPMs allow for a sampling rate of up to 100 MHz for the incident rate of converted photons to optical photons. When combined with a fast scintillator, e.g., LYSO, GOS, LSO, and the like, even single photon detection with energy discrimination is possible, which provides important additional diagnostic information.

Figure 2:
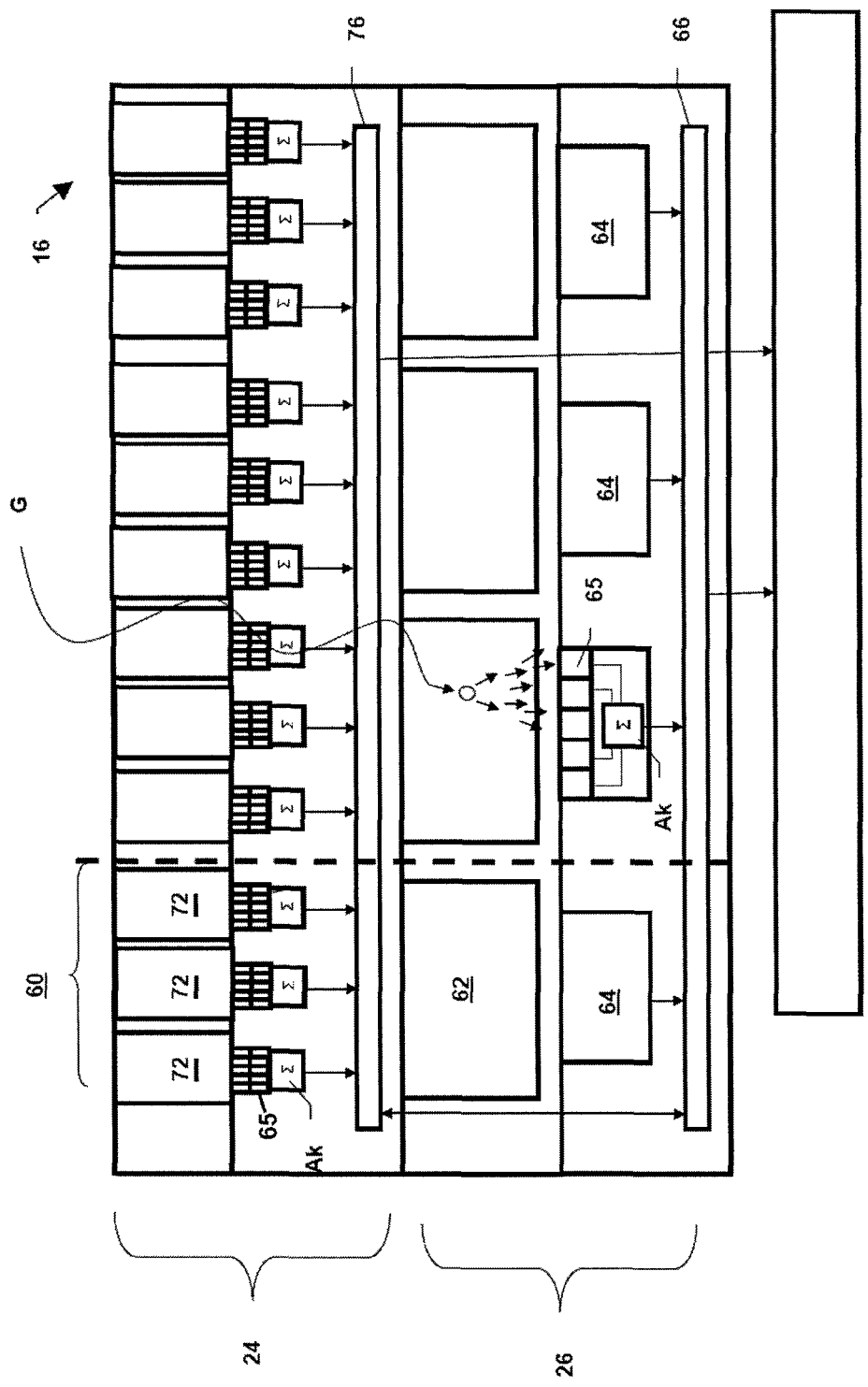
FIG. 2 illustrates an exemplary segment of a detector array according to one aspect of the present disclosure.
Figure 3:
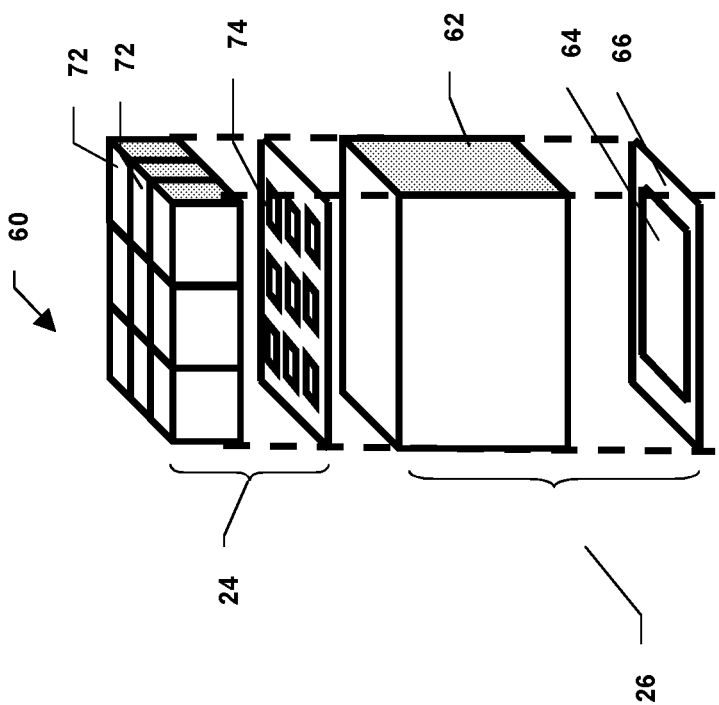
FIG. 3 is an expanded view of a detection assembly for one PET detector and nine CT detectors.

With reference to FIGS. 2 and 3, the detector array 16 includes a plurality of detector cells 60 which, in the illustrated embodiment, each include one PET detector and nine CT detectors. In the illustrated embodiment, the second detector layer 24 includes an array of PET detectors which each includes a scintillator 62 which, in the illustrated embodiment, is about 4 mm×4 mm to generate a PET image with a 4 mm$^3$ resolution. Other sizes such as in the 2.8×2.8-8×8 mm$^3$ ranges are also contemplated. The scintillator has a sufficient thickness that substantially all of the PET gamma rays G are stopped and turned into light, e.g., about 2.8-8 mm for 511 keV radiation. Five of the six faces of the PET scintillator are coated with a light transmission blocking, reflective layer. The sixth surface, the bottom surface in the illustrated embodiment, is optically coupled to a light detector 64. In the illustrated embodiment, the light detector 64 includes one or more arrays 65 of silicon photomultipliers (SiPMs). The outputs from the SiPMs are summed by a concentrator Ak and conveyed to a processing layer 66 which conveys the PET data to evaluation modules. The light detectors are associated in a one-to-one manner to corresponding scintillator elements, though this need not necessarily be the case. As shown for one light detector only, each light detector comprises a plurality of "cells". The detection signals of all detector cells of each light detector are communicated to a concentrator network Ak, where the total numbers of detected particles during annihilation events or optic photon generation are determined as a digital value.

The first layer 24 includes an array of CT detectors supported on a radiation receiving face of the scintillators 62 of a corresponding PET detector. In the illustrated embodiment, there are nine CT detectors which overlay each PET detector. For simplicity of construction, the PET detectors have a cross-section which is substantially an integer multiple of the cross-sectional dimensions of the CT detectors but this is not required. Each CT detector, as illustrated in FIG. 3, includes a scintillation crystal 72 which is covered on five of its six sides by a light impermeable, reflective layer (not shown). A corresponding light detector 74 is optically coupled to each scintillator. Again, the light detector 74 in the illustrated embodiment includes one or more arrays 65 of SiPMs. The CT detector scintillators 72 each have a thickness which stops at least a large portion of the CT radiation, e.g., about 1-4 mm. The scintillators in the illustrated embodiment are about 1.4×1.4 mm$^2$ to generate CT images with voxels 1.4 mm$^3$. Other sizes are also contemplated. Each of the light detectors 74 is connected with a wiring layer 76 as illustrated in FIG. 2, which may include or be electrically connected with evaluation modules. In the illustrated embodiment, each light detector includes an array of SiPMs connected with a concentrator Ak.

Although the light detectors 64, 74 are illustrated as being optically coupled to the lower surface of each scintillator, it is to be contemplated that the light detectors could be connected to other surfaces, such as one or more side surfaces.

Because PET radiation has higher energy (about 511 keV) and the CT radiation has lower energy (about 20-140 keV), the CT radiation is preferentially stopped in the CT scintillators and the PET radiation traverse the CT scintillators with few interactions. Data from any scintillations in the PET scintillators during CT imaging can be ignored. Any PET gamma ray interactions in the CT scintillators can be used during PET imaging to derive depth of interaction information.

In order to determine depth of interaction information, the outputs of each array of the nine CT detectors (in the illustrated embodiment) can be coupled together and treated like a single PET detector during PET imaging. Scintillations from the PET gamma rays occurring in the first layer of CT scintillators 72 are then known to have occurred with a depth of interaction between zero and the thickness of the CT scintillators. Scintillations detected in the PET scintillator 62 are then known to have a depth of interaction between a depth equal to the thickness of the CT scintillators (plus an equivalent depth contributed by the light detector array 74) and to the thickness of the PET detector scintillator plus the CT scintillator. For example, the CT scintillators can be 4 mm thick and the PET scanners 4 mm thick to provide depth of interaction information for the PET radiation.

Figure 4:
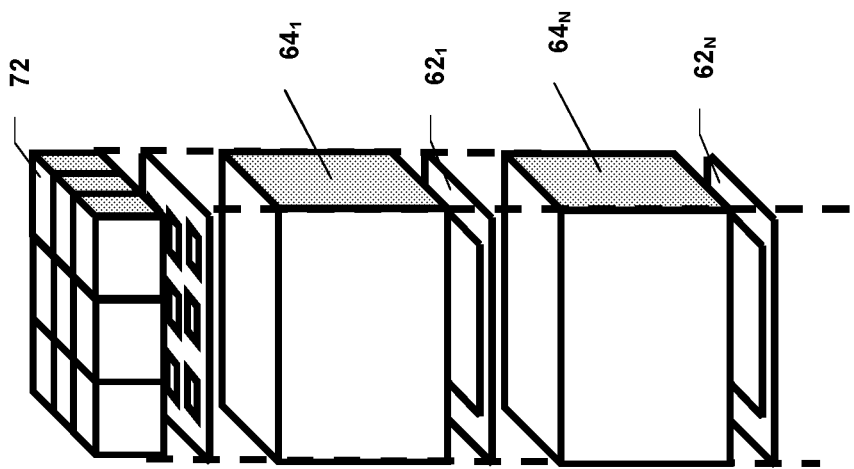
FIG. 4 is similar to FIG. 3, but with the PET detector configured for three levels of depth of interaction information.

As illustrated in FIG. 4, rather than a single PET detector, the PET detector may be divided into N PET detectors, where N is a plural integer. By selecting appropriate thickness for the CT and PET scintillators, depth of interaction data can be generated for each of N+1 depth ranges. That is, the group of CT detectors that overlay the scintillator $62_1$ of a first PET detector are grouped together to define the first depth range. The scintillator $62_1$ defines the second depth range. N additional scintillators $64_N$ of N additional PET detectors are aligned with the first PET scintillator $64_1$ to define the third through Nth depth ranges.

Figure 5:
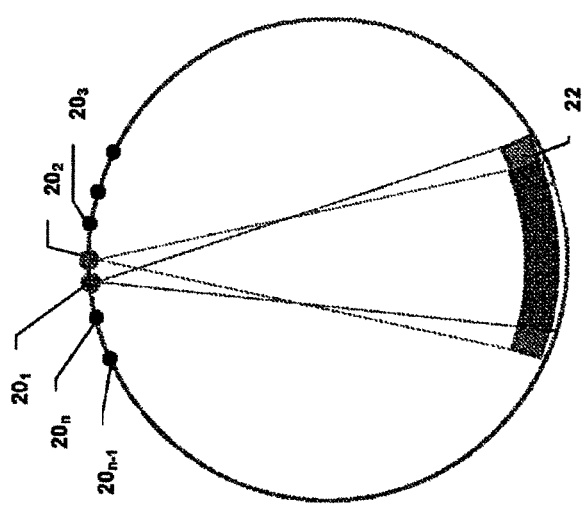
FIG. 5 illustrates a cross sectional view of an alternate embodiment with a plurality of distributed x-ray sources and a rotating anti-scatter grid.

In one embodiment illustrated in FIG. 5, the x-ray source includes n distributed x-ray sources $20_1, \ldots, 20_n$, where n is a plural integer, surrounding the patient around the circumference of the examination region. For example, by sequentially activating the x-ray sources, an active region moves around the examination while that x-ray source remains stationary. The x-ray sources can include, for example, carbon nanotubes (CNTs). In this example, the ASG 22 rotates to be opposite each source as it is activated to focus the x-rays on the detector array.

CT imaging uses projection images from different viewing angles. Conventional systems use a moving x-ray source to acquire the individual projections. Using a stationary distributed x-ray source with a number of sources that equals the number of projections is achieved without mechanical motion. Advantages are a potentially faster image acquisition speed, higher spatial and temporal resolution and simpler system design. Carbon nanotubes (CNTs) have field emission cathodes that deliver the electrons at an active focus region, which rotates around for x-ray production. CNT emitters feature a stable emission at a high current density, a cold emission, excellent temporal control of the emitted electrons, and good configurability. The anti-scatter grid 22 is rotated to remain diametrically opposing the active focus region of the CNTs to reduce scattering of radiation on detector 24 and produce sharper images. The scattering is reduced when the radiation impacting the detector is from a limited small angle.

Figure 6:
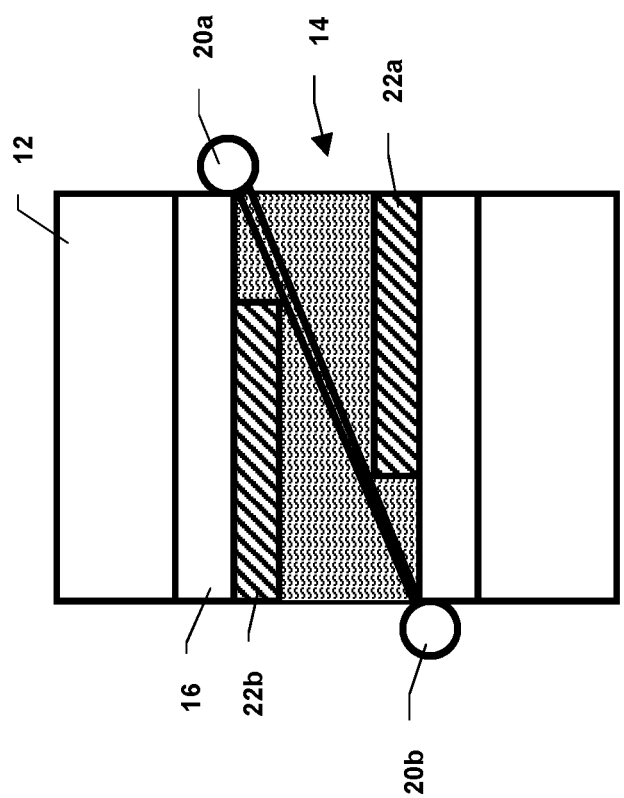
FIG. 6 illustrates another embodiment in which x-ray sources are disposed on both ends of the examination region.

In another embodiment illustrated in FIG. 6, x-ray sources 20a, 20b are mounted on opposite ends of the examination region 14. Each x-ray source, either rotating or distributed, has an associated ASG 22a, 22b that rotates with it. By angularly offsetting the x-ray sources and ASGs by an angle greater than a maximum fan angle of the x-ray sources, mechanical interference between the ASGs can be reduced or eliminated. In one embodiment, the ASG 22a, 22b has a rest position in which the ASG can be moved, electronically, mechanically, manually or otherwise, out of the examination region. In addition, injection can alternatively occur prior to scanning.

Figure 7:
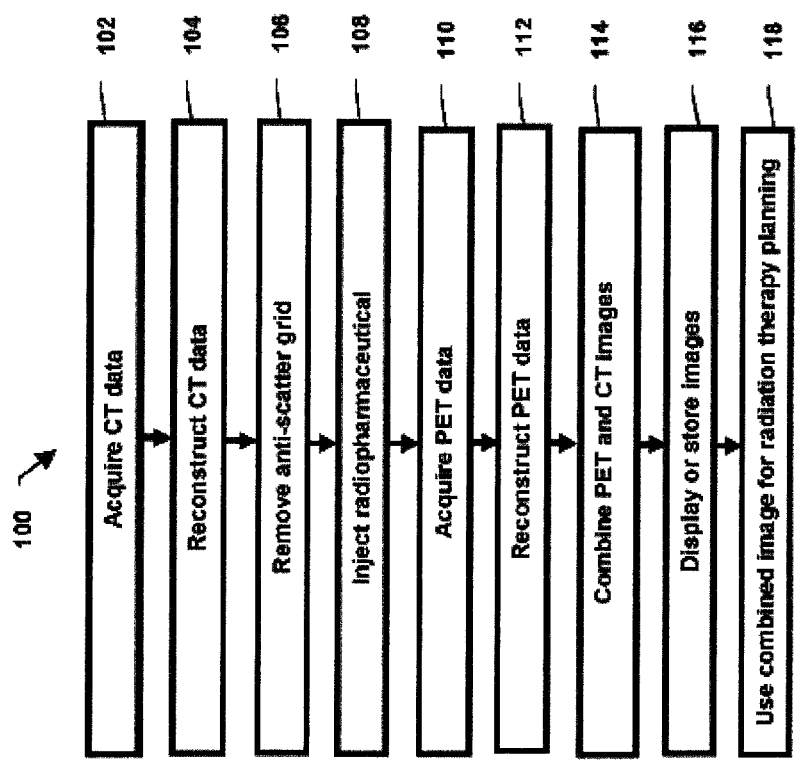
FIG. 7 diagrammatically shows a suitable method for an imaging system with a single detector illustrated in FIG. 2.

One embodiment of a methodology 100 for detecting radiation in a hybrid PET/CT scanner system is illustrated in FIG. 7. While the method 100 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 102, the acquisition controller 34 acquires the CT data from the first detector layer 24. The acquisition controller 34 obtains acquisition parameters 36 that are stored in the CT data buffer 38. At 104, a CT images is reconstructed by the CT reconstruction engine 40. At 106, the anti-scatter grid is removed from the examination region 14. At 108, the patient is injected with the radiopharmaceutical to be imaged during PET scanning.

At 110, the acquisition controller 34 obtains the PET acquisition parameters and the PET data is acquired and stored in the list mode. The acquisition of PET data can be started while the CT data is being reconstructed. In a concurrent mode, the PET and CT data are acquired concurrently; due to the high energy difference between PET and CT photons, the ASG optimized for the (low energy) CT photons may not significantly affect the 511 keV photons of PET. In the concurrent mode, it may be advantageous to eliminate the anti-scatter grid such that it does not interfere with the acquisition of the PET data. Alternately, the PET data can be appropriately adjusted to compensate for the anti-scatter grid.

At 112, the PET reconstruction engine 46 reconstructs the PET data into PET images. The CT image can be used as an attenuation map in the PET reconstruction.

At 114, the PET and CT images are combined. Because the PET and CT images are taken with the same detector arrays, the PET and CT images are inherently aligned and complex registration algorithms may not be required. At 116, the combined image and/or the PET and CT images are displayed on the display 56 or stored in temporary storage or hospital archives as part of the patient's record. At 118, the combined or other images are used as an input for further processing or functions. For example, the combined image can be used in a radiation therapy planning procedure. This application has described one or more preferred embodiments.

Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A radiation detector system comprising:
   a first detector layer of detectors having a first cross-section dimension and to convert incident radiation from transmission source into transmission data or emission radiation into emission data wherein the first detector layer includes an array of first scintillators and an array of first photodetectors;

at least one second detector layer of detectors having a second cross-section dimension and disposed below the first layer to convert emission radiation into emission data wherein the second detector layer includes an array of second scintillators and an array of second photodetectors; and
a processor connected with the first and at least one second detector layers and programmed to:
perform CT imaging using transmission data acquired by the first detector layer including the first scintillators while ignoring any scintillations in the second scintillators; and
perform emission imaging using at least emission data acquired by the at least one second detector layer including the second scintillators.

2. The system according to claim 1, wherein each detector of the second detector layer is overlaid by a group of the detectors of the first detector layer which are configured to output separately in a transmission imaging mode and are configured with their outputs coupled together to operate as a single detector in an emission imaging mode.

3. The system according to claim 1, wherein the second cross-section dimension is an integer multiple of the first cross-section dimension.

4. The system according to claim 1, wherein the first detector array and the second detector array each include avalanche photodiode arrays optically coupled to the first and second scintillators, respectively.

5. The system according to claim 1, further including:
one or more additional detector arrays having emission radiation detectors that are aligned with corresponding detectors of the second detector layer.

6. The system according to claim 1, further including:
an anti-scatter grid that rotates between a subject and the detector around the examination region opposite of an active focus region of carbon nanotubes.

7. The system according to claim 1, wherein the processor is programmed to perform emission imaging using both emission data acquired by the at least one second detector layer including the second scintillators and emission data acquired by the first detector layer including the first scintillators.

8. An imaging system comprising:
a gantry that defines an examination region;
a plurality of the detector systems according to claim 1, disposed around the examination region;
at least one transmission radiation source;
at least one reconstruction engine which reconstructs the transmission data into an anatomical image and the emission data into a functional image.

9. The system according to claim 8, wherein the transmission radiation source is an x-ray source and the emission data is PET data and the first detector layer acquires CT data and includes a group of CT detectors electronically coupled together to operate as a PET detector and acquires PET data.

10. The imaging system (10) according to claim 8, wherein the transmission source rotates with an anti-scatter grid relative to the examination region to acquire the transmission data.

11. The imaging system according to claim 8, wherein the transmission source includes a plurality of stationary distributed x-ray sources distributed around a circumference of the examination region.

12. The imaging system according to claim 11, further including:
an anti-scatter grid that rotates around the examination region opposite of an active focus region of the stationary distributed x-ray sources.

13. A method comprising:
providing a multi-layer detector having a first detector layer proximate to an examination region and a second detector layer distal from the examination region with the first detector layer disposed between the examination region and the second detector layer;
converting incident radiation from a transmission radiation source into transmission data at first detectors of the first detector layer while ignoring any conversion of incident radiation from the transmission source into transmission data at second detectors of the second detector layer; and
converting emission radiation into emission data at the second detectors of the second detector layer.

14. The method according to claim 13, wherein the emission data are collected in a list-mode and further including:
reconstructing the emission data set to generate a functional image.

15. The method according to claim 13, wherein the first and second detector layers encircle an examination region and further including:
rotating an anti-scatter grid which rotates around the examination region during the converting of the transmission radiation into transmission data.

16. The method according to claim 15, further including:
rotating the transmission radiation source around the examination region in coordination with the rotating of the anti-scatter grid.

17. The method according to claim 15, wherein the transmission radiation source includes a plurality of distributed radiation sources stationarily mounted and the examination region and further including:
sequentially activating the distributed radiation sources in coordination with the rotation of the anti-scatter grid.

18. A hybrid transmission and emission radiation imaging system comprising:
a gantry which defines an examination region;
at least one transmission radiation source disposed adjacent the examination region to irradiate at least a portion of the examination region;
a plurality of detectors disposed around the examination region, each detector including:
a first array of scintillators disposed to receive emission radiation from a subject in the examination region and the transmission radiation from the at least one transmission radiation source, the scintillators of the first array of scintillators having a thickness sized to stop the transmission radiation and having a first cross section,
a first array of optical detectors, at least one of the optical detectors being optically coupled with each scintillator of the first scintillator array to generate transmission and emission data,
a second array of scintillators disposed with the first array of scintillators interposed between the examination region and the second array of scintillators to receive emission radiation which passed through the first array of scintillators, the scintillators of the second array having a second cross section larger than the first cross section,
a second array of optical detectors, at least one optical detector of the second array of optical detectors being optically coupled with each scintillator of the second scintillator array to generate emission data; and a reconstruction processor programmed to convert the emission data from the first and second detector arrays into an emission image representation and to convert the transmission data from the first detector array into a transmission image while ignoring any scintillations in the second array of scintillators;

wherein the hybrid transmission and emission radiation imaging system has:

a transmission imaging mode in which the first array of optical detectors are configured generate transmission data with a first resolution corresponding to the first cross sectional dimension; and an emission imaging mode in which groups of optical detectors of the first array of optical detectors are wired together to generate emission data with a second resolution corresponding to the second cross sectional dimension.

* * * * *